United States Patent [19]

Kirsch

[11] Patent Number: 5,591,234
[45] Date of Patent: Jan. 7, 1997

[54] POST-SURGERY ORTHOPEDIC COVERING

[75] Inventor: Axel Kirsch, Talstrasse 23, D70794 Filderstadt, Germany

[73] Assignee: Axel Kirsch, Filderstadt, Germany

[21] Appl. No.: 530,009

[22] Filed: Sep. 19, 1995

Related U.S. Application Data

[63] Continuation of Ser. No. 188,490, Jan. 28, 1994, abandoned.

[30] Foreign Application Priority Data

Feb. 1, 1993 [DE] Germany .......................... 43 02 709.1

[51] Int. Cl.⁶ ..................................................... A61F 2/28
[52] U.S. Cl. .................................. 623/16; 623/11; 606/70; 606/77
[58] Field of Search .................................. 623/11, 16, 18, 623/20, 22, 23; 606/69–71, 76–77, 92; 604/304; 602/41, 44

[56] References Cited

U.S. PATENT DOCUMENTS

| | | |
|---|---|---|
| 4,145,468 | 3/1979 | Mizoguchi et al. . |
| 4,365,357 | 12/1982 | Draenert ..................................... 623/18 |
| 4,539,981 | 9/1985 | Tunc ........................................... 606/77 |
| 4,801,299 | 1/1989 | Brendel et al. . |
| 4,813,958 | 3/1989 | Dixon . |
| 4,816,339 | 3/1989 | Tu et al. . |
| 5,007,916 | 4/1991 | Linsky et al. . |
| 5,057,111 | 10/1991 | Park . |
| 5,196,016 | 3/1993 | Buser et al. ............................... 606/76 |
| 5,346,492 | 9/1994 | Morgan ..................................... 623/16 |
| 5,380,328 | 1/1995 | Morgan ..................................... 606/70 |

FOREIGN PATENT DOCUMENTS

| | | |
|---|---|---|
| 0082621 | 12/1982 | European Pat. Off. . |
| 0190422 | 8/1986 | European Pat. Off. ................. 623/18 |
| 0189546 | 8/1986 | European Pat. Off. ................. 623/18 |
| 0475077 | 8/1991 | European Pat. Off. . |
| 0504103 | 2/1992 | European Pat. Off. . |
| 3831657 | 3/1990 | Germany ................................. 606/77 |
| 3901811 | 4/1990 | Germany ................................. 606/70 |
| 9115341.7 | 4/1992 | Germany . |
| 0581935 | 11/1977 | U.S.S.R. ............................... 623/16 E |
| 2056882 | 3/1981 | United Kingdom ................. 623/16 G |
| 2142544 | 1/1985 | United Kingdom ..................... 623/16 |
| 8700419 | 1/1987 | WIPO ..................................... 606/76 |
| WO90/01955 | 3/1990 | WIPO . |

*Primary Examiner*—Debra S. Brittingham
*Assistant Examiner*—P. Zuttarelli
*Attorney, Agent, or Firm*—Hill, Steadman & Simpson

[57] ABSTRACT

A post-surgery orthopedic covering for a recess in endogenic bone tissue filled with an osteogenic material, such as hydroxyapatite granules, has a covering membrane with a stiffening layer which can be integrated with the covering membrane, or provided as a separate stiffening element.

22 Claims, 1 Drawing Sheet

POST-SURGERY ORTHOPEDIC COVERING

This is a continuation, of application Ser. No. 08/188,490, filed Jan. 28, 1994, now abandoned.

BACKGROUND OF THE INVENTION

1. Field of the Invention

The present invention relates to membranes of the type employed for the temporarily covering a recess in the endogenic bone tissue filled with an osteogenic material, such as hydroxyapatite granules.

2. Description of the Prior Art

Following bone surgery, for example, in the reconstruction of bones in plastic surgery or in the case of operations on the jaw, it is standard practice to fill the bone defect or deficiency points, which are in the form of recesses or cavities in the endogenic bone tissue, with an osteogenic material. Such osteogenic material generally consists of a mixture of bone replacement material, such as hydroxyapatite granules and endogenic bone particles. To ensure that the osteogenic material grows substantially exclusively in an osseous manner from the bone side, but does not grow into surrounding mucous tissue, the recess is closed with a covering membrane of the type generally described above. The purpose of such a membrane is to ensure that there is no growth of the osteogenic material into the non-bone tissue. Only by ensuring complete osseous growth of the osteogenic material is it possible to substantially completely eliminate the bone defect point, and to reintegrate the osteogenic material into the endogenic bone after osseous growth has taken place.

Heretofore, polytetrafluoroethylene films have been used as such covering membranes, however, such known membranes have the disadvantage of remaining in the body when the bone defect point heals, and can therefore create complications.

As a result of the material used for conventional covering membranes, such as, for example, plastic films, the membrane is not stiff and can therefore change its position as a result of radial stressing transmitted through the surrounding soft body tissue as a result, for example, of muscular movements. Such movements of the covering membrane have the disadvantage that the transfer of the blood clot in the bone defect point into the bone tissue is impaired, because the portion of the osteogenic material which is near the membrane, or the portion of the blood clot which is near the membrane, is disturbed by the covering membrane movement.

SUMMARY OF THE INVENTION

It is an object of the present invention to provide a post-surgery orthopedic covering of the type having a membrane, adapted to cover a recess in endogenic bone tissue filled with osteogenic material, wherein the undisturbed transfer of the osteogenic material or blood clot in the bone defect point into the bone tissue is not disturbed.

It is a further object of the present invention to provide such a covering wherein it is avoided that membrane material left in the body following the healing of the bone defect point will result in complications.

The above objects are achieved in accordance with the principles of the present invention in a post-surgery orthopedic covering having a membrane adapted to cover a recess in endogenic bone tissue filled with osteogenic material, wherein the membrane has a stiffening layer associated therewith. The stiffening layer can be integrated into the membrane itself, or can be constructed as a stiffening element separate from the membrane. The stiffening layer is located on or within the membrane at a side thereof remote from the endogenic bone tissue.

The stiffening layer can be formed by a perforated metal plate, a metal lattice, or metal gauze.

The stiffening layer may be made from titanium, or in a further embodiment the stiffening layer can be made from plastic. The stiffening layer may be in the form of a plastic grid.

In a further embodiment of the invention, the membrane material is also a plastic material, however, the plastic material of the stiffening layer is different from the plastic material used to form the membrane.

The stiffening layer in the covering of the invention has a thickness in the range of 0.3 to 1.0 mm, and preferably has a thickness of approximately 0.5 mm.

The membrane may consist of material which is absorbable or resorbable into the body.

The membrane material can be made more rapidly resorbable from a side remote from the endogenic bone than from the side facing the endogenic bone. The membrane material density can increase from the side remote from the endogenic bone to the side facing the endogenic bone.

The membrane material may be formed by several layers of different densities and/or compositions in order to achieve the aforementioned resorbability and/or density gradients.

The membrane material may include several woven or knitted layers of different texture (i.e., different openness of weave).

The membrane material can consist at least partly of lyophilized dura mater. The membrane material may at least partly consist of polylactide/vicryl.

The membrane material may at least partially comprise collagen, or can partly comprise polylactide.

The membrane material may partly comprise oxymethyl cellulose.

The resorbability gradient of the membrane material may be set so as to decrease from the side thereof remote from the endogenic bone to the side facing the endogenic bone by making the membrane material layer which engages the bone resorbable by the endogenic tissue only when the recess of the endogenic bone closed by the covering membrane has been substantially completely ossified, so that the recess or fracture has substantially closed.

The invention is based on the discovery that it is possible to ensure a satisfactory transfer of the osteogenic material, or the blood clot enclosing it, in the bone defect point into the osseous tissue by preventing covering membrane movements by means of a stiffening layer. The stiffening layer ensures that the blood clot is transferred in an undisturbed manner into the bone tissue.

DESCRIPTION OF THE PREFERRED EMBODIMENTS

Figure 1:
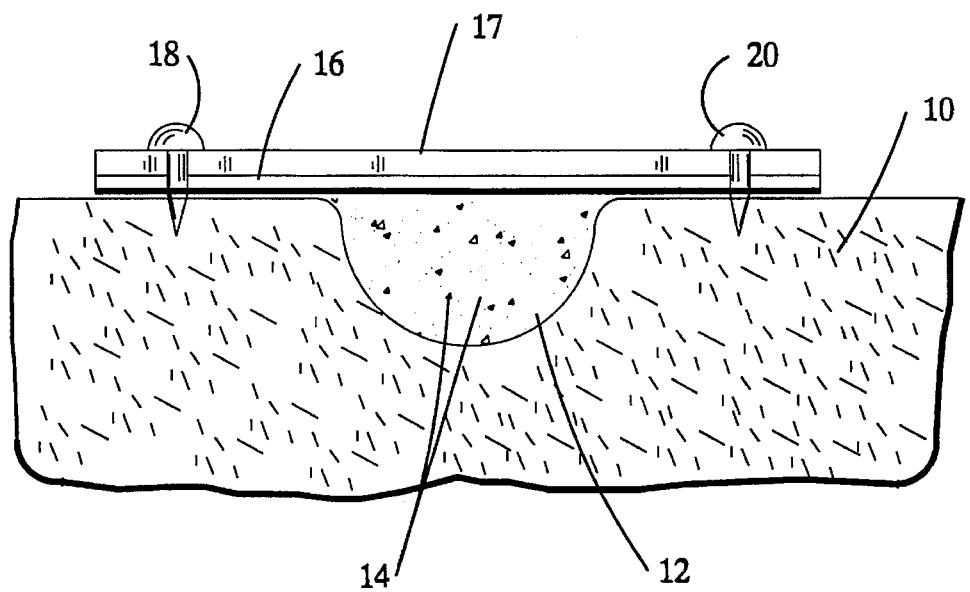
FIG. 1 is a schematic, side view of a bone defect point covered by a post-surgery orthopedic covering constructed in accordance with the principles of the present invention, shown in section at a right angle to the plane of the covering.
Figure 2:
FIG. 2 is a sectional view of a stiffening layer of the covering shown in FIG. 1, in a section at a right angle to the plane of the covering, and shown enlarged in comparison to FIG. 1.

As shown in FIG. 1, a bone defect point characterized by a recess 12 in an endogenic bone is substantially completely filled with osteogenic material 14, such as hydroxyapatite granules, which are admixed in a known manner with bone particles comprising endogenic bone tissue. The recess 12 filled with the osteogenic material 14 is covered by a covering membrane 16, which is tightly engaged on the endogenic bone 10 completely surrounding the recess 12 by means of fixing pins 18 and 20. The function of the covering membrane 16 is to ensure the osseous growth of the osteogenic material 14 from the endogenic bone 10, in such a manner that contamination of the osteogenic material 14 with anything other than bone tissue, such as with mucous tissue, is prevented. The membrane 16 is provided with a stiffening layer 17 at a side thereof remote from the endogenic bone tissue 10. As shown in FIG. 2, the stiffening layer 17 may be formed by a perforated titanium sheet, the thickness of which may be, for example, 0.5 mm. The perforated metal sheet forming the stiffening layer 17 stiffens the covering membrane 16 such that, in the event of movements of the tissue surrounding the endogenic bone 10, no relative motion of the covering membrane 16 in relation to the osteogenic material 14 occurs, nor does any movement of the covering membrane 16 relative to the blood clot filling the recess 12 take place. The blood clot can thereby be absorbed into the bone tissue without the risk of a non-uniform distribution, which may result in a non-uniform growth pattern.

Figure 3:
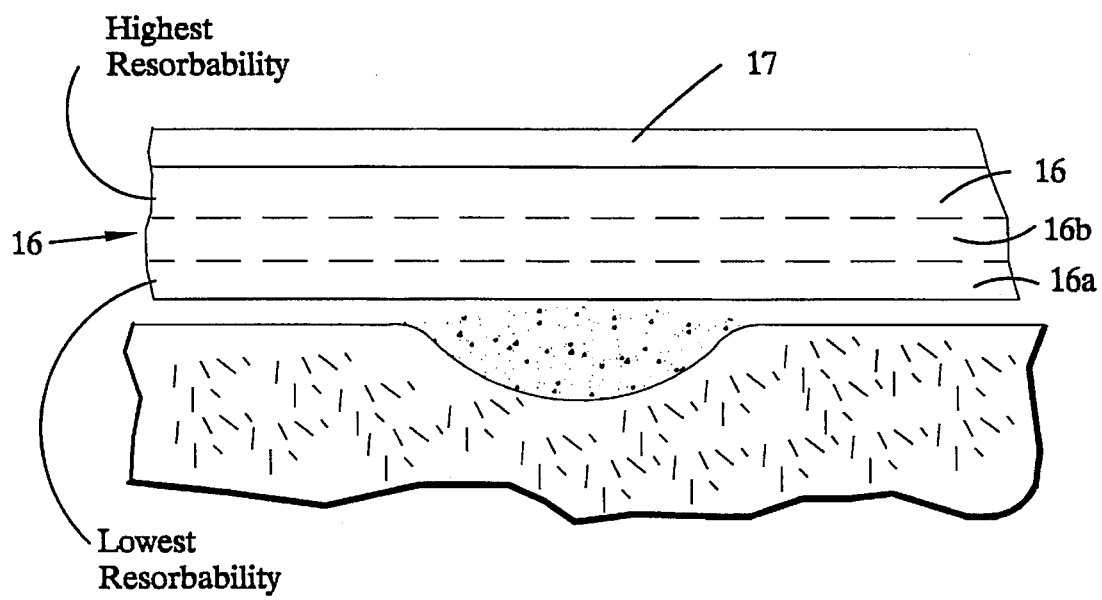
FIG. 3 is a schematic, enlarged view of the post-surgery orthopedic covering of FIG. 1, illustrating the composition of the membrane 16 as being formed by a number of layers.

As shown in FIG. 3, the membrane 16 is formed by a number of different layers, with three layers 16a, 16b and 16c being shown in the exemplary embodiment, however, any suitable number of layers may be employed. The layers have different mechanical properties, such as different densities, different weaves, different texture, etc., so that the membrane material exhibits a resorbability gradient which increases from a side remote from the endogenic bone (layer 16c) to a side facing the endogenic bone (layer 16a).

Although modifications and changes may be suggested by those skilled in the art, it is the intention of the inventor to embody within the patent warranted hereon all changes and modifications as reasonably and properly come within the scope of his contribution to the art.

I claim as my invention:

1. A post-surgery orthopedic covering adapted to cover a bone defect point in endogenic bone tissue filled with an osteogenic material, said covering comprising:

a membrane adapted to be disposed adjacent said bone defect point and said endogenic bone tissue;

a stiffening layer connected to said membrane;

said membrane consisting of resorbable membrane material and comprising a plurality of layers having respectively different mechanical properties, giving said layers, in combination, a resorbability gradient from a first side of said membrane adapted to be remote from said endogenic bone to a second side of said membrane adapted to face said endogenic bone, said resorbability gradient increasing from said first side to said second side.

2. A covering as claimed in claim 1 wherein said stiffening layer is integrated into said membrane.

3. A covering as claimed in claim 1 wherein said stiffening layer comprises a stiffening element separate from said membrane.

4. A covering as claimed in claim 3 wherein said stiffening layer connected at a side of said membrane adapted to be remote from said endogenic bone tissue.

5. A covering as claimed in claim 1 wherein said stiffening layer consists of a perforated metal plate.

6. A covering as claimed in claim 1 wherein said stiffening layer comprises a metal lattice.

7. A covering as claimed in claim 1 wherein said stiffening layer comprises metal gauze.

8. A covering as claimed in claim 1 wherein said stiffening layer consists of titanium.

9. A covering as claimed in claim 1 wherein said stiffening layer consists of plastic.

10. A covering as claimed in claim 1 wherein said stiffening layer consists of a plastic grid.

11. A covering as claimed in claim 1 wherein said membrane consists of first plastic material and wherein said stiffening layer consists of a second plastic material different from said first plastic material.

12. A covering as claimed in claim 1 wherein said stiffening layer has a thickness in a range of 0.3 to 1.0 mm.

13. A covering as claimed in claim 12 wherein said stiffening layer has a thickness of approximately 0.5 mm.

14. A covering as claimed in claim 1 wherein said membrane consists of a plurality of layers having respectively different compositions.

15. A covering as claimed in claim 1 wherein said membrane consists of a plurality of layers having respectively different densities.

16. A covering as claimed in claim 1 wherein said layers consist of woven material with respectively different weave openness.

17. A covering as claimed in claim 1 wherein said resorbable material of said membrane includes lyophilized dura mater.

18. A covering as claimed in claim 1 wherein said resorbable material of said membrane includes polylactide/ vicryl.

19. A covering as claimed in claim 1 wherein said resorbable material of said membrane includes collagen.

20. A covering as claimed in claim 1 wherein said resorbable material of said membrane includes polylactide.

21. A covering as claimed in claim 1 wherein said resorbable material of said membrane includes oxymethyl cellulose.

22. A covering as claimed in claim 1 wherein said resorbability gradient decreases from said side of said membrane adapted to be remote from said endogenic bone to said side of said membrane adapted to face said endogenic bone so that said membrane material at said side adapted to face said endogenic bone is only resorbed by said endogenic bone when substantially complete osseous growth in said recess has occurred.

* * * * *